US00PP16938P2

(12) United States Plant Patent
Kordes

(10) Patent No.: US PP16,938 P2
(45) Date of Patent: Aug. 1, 2006

(54) CLIMBING ROSE PLANT NAMED 'KORKLEMOL'

(50) Latin Name: *Rosa hybrida*
Varietal Denomination: KORklemol

(75) Inventor: Tim-Hermann Kordes, Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 11/071,754

(22) Filed: Mar. 2, 2005

(51) Int. Cl.
*A01H 5/00* (2006.01)

(52) U.S. Cl. ..... Plt./109

(58) Field of Classification Search ..... Plt./109, Plt./111, 112, 113
See application file for complete search history.

(56) References Cited

PUBLICATIONS

Gemman PBR Application ROS 2449 Apr. 5, 2004 W. Kordes' Söhne.
QZ (CPVO) Applicaton 20041560 Aug. 19, 2004 W. Kordes' Söhne.

*Primary Examiner*—Kent Bell
*Assistant Examiner*—June Hwu

(57) ABSTRACT

A new and distinct variety of rose with abundant, novel copper to yellow flowers, and attractive foliage with very good disease resistance. It exhibits vigorous growth and an upright climbing habit. The new variety propagates well from traditional methods. This new and distinct variety has shown to be uniform and stable in the resulting generations from asexual propagation.

1 Drawing Sheet

CROSS REFERENCES AND FEDERAL R&D STATEMENT

There are no cross referenced or related applications. This variety was developed without the aid of any research grant.

Latin name of genus and species: The botanical classification of the new rose plant is *Rosa hybrida*.

Variety denomination: The denomination of the new variety is 'KORklemol'.

BACKGROUND OF THE INVENTION

The new variety of rose plant of the present invention originated from a controlled crossing in a breeding program of two distinct parents during the summer of 1994. The crossing was between un-named seedling, a non-patented rose by the same inventor and an un-named seedling, a non-patented rose also by the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORklemol'.

SUMMARY OF THE INVENTION

The new rose plant may be distinguished from its seed parent, an un-named seedling which had resulted from a crossing with another un-named seedling and Lichtkönigin Lucia, by the following combination of characteristics:

1. 'KORklemol' is more vigorous, and
2. the flowers of 'KORklemol' have a stronger fragrance and a lighter color.

The new rose plant may be distinguished from its pollen parent, an un-named seedling by the following combination of characteristics:

1. 'KORklemol' has few petals, and
2. 'KORklemol' has a stronger fragrance and a deeper color.

The objective of the hybridization was to create a new and distinct rose plant with unique qualities, such as:

1. Vigorous upright growth;
2. Abundant attractive, recurrent flowers;
3. Attractive and abundant foliage; and
4. Resistance to diseases encountered in landscapes and gardens.

This combination of qualities is not present in prior rose cultivars. These objectives have been substantially achieved and in that distinguish 'KORklemol' from all other varieties of which we are aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORklemol'was selected in May, 1995 from the seedling beds to be asexually propagated for further evaluation. The first asexual propagation of 'KORklemol' was done by budding to seedling understocks in July, 1995 at the W. Kordes Söhne Nursery in Offenseth-Sparrieshoop, Germany.

This initial and other subsequent propagations conducted in controlled environments show that the foregoing and all other characteristics of 'KORklemol' come true to form and are transmitted through succeeding generations.

BRIEF DESCRIPTION OF THE DRAWING

The accompanying color illustration shows as true as is reasonably possible to obtain in color photographs of this type, the typical characteristics of the buds, flowers, and leaves of 'KORklemol'. Specifically illustrated in SHEET ONE are flower buds and open blooms of the variety.

DETAILED BOTANICAL DESCRIPTION

The following is a description of 'KORklemol', as observed in its growth in a nursery in Jackson County, Oreg. on plants of 1 year of age and in its growth on 3 year old plants in a field nursery in Sparrieshoop, Germany. Color references are made using The Royal Horticultural Society (London, England) Colour Chart, 2001 except where common terms of color are used.

For a comparison, several physical characteristics of the rose variety 'KORhoro' a rose variety from the same inventor in Chart 1.

CHART 1

| Characteristic: | 'KORklemol' | 'KORhoro' |
|---|---|---|
| Petal count | 20 petals. | 25–30 petals. |
| Flower color | Light yellow. | Dark yellow. |
| Scent | Abundant. Fruity. | Little or no fragrance. |

Parents:

*Seed parent.*—Un-named seedling.

*Pollen parent.*—Un-named seedling.

Classification:

*Botanical classification.*—*Rosa hybrida*, 'KORklemol'.

*Commercial classification.*—Climbing rose.

FLOWER AND FLOWER BUD

Blooming habit: Recurrent flowering.

Flower bud:

*Size.*—Upon opening, 30–40 mm in length from base of receptacle to end of bud.

*Bud form.*—Pointed ovoid to ovoid.

*Bud color.*—As sepals first unfold, bud color is Orange Group 26A. When ¼ open, the upper surface of petals is Orange Group 26C, and the lower surface is Orange Group 26B.

*Sepals.*—Size: Relatively small and short. Average 12 mm long×6 mm wide. Shape: Weak foliaceous appendages on three of the five sepals. Sepal apex is cirrose. Base is flat at union with receptacle. Quantity: Five. Surface texture: Outer surface with a few white hairs. Upper surface pubescent. Limited numbers of stipitate glands are present, principally on the sepal margins. Color: Upper surface Green Group 138A. Lower surface Green Group 138A.

Receptacle:

*Surface.*—Nearly smooth, with some fine hairs.

*Color.*—Green Group 138A.

*Shape.*—Funnel.

*Size.*—6 mm (h)×8 mm (w).

Peduncle:

*Surface.*—Near smooth with some stipitate glands.

*Length.*—40–60 mm average length.

*Diameter.*—2.0–3.0 mm average diameter.

*Color.*—Green Group 138A with intonations of Red-Purple Group 183C.

*Strength.*—Strong.

*Borne.*—Multiple flower buds per stem, generally 6 to 8.

Flower bloom:

*Fragrance.*—Strong, with tones of fruit and spice.

*Duration.*—On the plant 3–5 days. Senesced petals drop away cleanly.

*Size.*—Medium flowered garden rose. Average flower diameter is 65–75 mm when open.

*Form.*—Shape of flower when viewed from the side: Upon opening, upper part: Flattened convex. Upon opening, lower part: Flattened convex. Open flower, upper part: Flat to flattened convex. Open flower, lower part: Flat to flattened convex.

Color:

*Upon opening, petals.*—Outermost petals: Outer Side: Yellow-Orange Group 17D. Intonations of Orange-Red Group N34B. Inner Side: Yellow-Orange Group 17C. Intonations of Orange-Red Group N34B, mostly on upper margin areas exposed to sun. Innermost petals: Outer Side: Yellow-Orange Group 17D. Inner Side: Yellow-Orange Group 17C.

*Upon opening, basal petal spots.*—Basal petal spot, outermost petals: Outer Side: Yellow Group 1D. Inner Side: Yellow Group 1D. Basal petal spot, innermost petals: Outer Side: Yellow Group 1D. Inner Side: Yellow Group 1D.

*After opening, petals.*—Outermost petals: Outermost petals: Outer Side: Yellow Group 8D. Intonations of Orange-Red Group N34B. Inner Side: Yellow Group 8C. Intonations of Orange-Red Group N34B, mostly on upper margin areas exposed to sun. Innermost petals: Outer Side: Yellow Group 8C. Inner Side: Yellow Group 8B.

*After opening, basal petal spots.*—Basal petal spot, outermost petals: Outer Side: Yellow Group 1D. Inner Side: Yellow Group 1D. Basal petal spot, innermost petals: Outer Side: Yellow Group 1D. Inner Side: Yellow Group 1D. Variegations: None observed.

General tonality: On open flower a blend of Yellow-Orange Group 13C and 13D, with some intonations of Orange-Red Group N34B. No change in the general tonality at the end of the $4^{th}$ day. Afterwards, general tonality is Yellow-Orange Group 13D.

Petals:

*Petal count.*—Double. Approximately 20–25 petals under normal conditions.

*Petal reflex.*—Petals reflex somewhat.

*Petal edge.*—Generally entire, however most petals with a point in the middle of the margin.

*Petal shape.*—Apex shape is round. Shape of base is acute.

*Petal size.*—25–30 mm long; 20–30 mm wide.

*Thickness.*—Average.

*Petal arrangement.*—Generally in a regular pattern with overlapping edges.

*Petaloids.*—Present. Average of 3–4 per flower. Petaloids are 6–8 mm long and 3–4 mm wide. Color of inner side is Yellow-Orange Group 13C. Color of outer side is Yellow-Orange Group 13C. Surface texture is smooth. Shape is linear to elliptic.

Reproductive organs:

*Pistils.*—Approximately 40–45 present. Stigmas: Location: Similar in position to anthers. Color: Green-Yellow Group 1A. Styles: Length: 10 mm long. Color: Green-Yellow Group 1A.

*Stamens.*—Approximately 40–45 in number. Anthers: Size: 1.5 mm long. Color: Yellow-Orange Group 14C. Pollen: Limited amounts present. Color: Brown Group 200D. Filaments: Color: Green-White Group 157B. Length: 8 mm.

THE PLANT

Plant growth: Vigorous. Upright climbing habit. When grown as a budded nursery plant the average plant height is 250 cm and the average plant width is 100 cm.

Stems:

*Stem color.*—Young wood: Green Group 138A. Older wood: Green Group 138A.

*Stem surface.*—Young wood: Smooth. Older wood: Smooth, with some ridges.

Prickles: Present.

*Incidence.*—5 per 10 cm of stem.

*Size.*—Average length: 4–6 mm.

*Color.*—Mature prickles colored Greyed-Orange Group 177D. Immature prickles colored Greyed-Red Group 179A. Prickles senesce to Greyed-Orange 177C.

*Shape.*—Deeply concave.

Leaves and leaflets: Normally 7 leaflets on normal leaves in middle of the stem.

*Leaf size.*—110 mm (l)×60–70 mm (w).

*Quantity.*—Abundant.

*Texture.*—Glossy.

*Color, mature foliage.*—Upper Leaf Surface: Green Group 139A. Lower Leaf Surface: Green Group 138A.

*Color, juvenile foliage.*—Upper Leaf Surface: Green Group 139A. Lower Leaf Surface: Green Group 138A.

*Anthocyanin intonation.*—Present. Limited intonations of near Greyed-Purple 183B present on undersides of developing leaflets, as well as on petioles, petiole rachis, and stems.

Stipules:

*Size.*—10–12 mm (l) — 5–6 mm (w).

*Stipule color.*—Green Group 139A.

*Presence of stipitate glands.*—Present on margins.

*Margins.*—Bearded. Margins serrated.

Petiole:

*Length.*—10–15 mm.

*Diameter.*—1.5 mm average diameter.

*Petiole color.*—Green Group 138A.

*Underneath.*—Smooth, with a few small prickles.

*Stipitate glands.*—Limited numbers present on margins.

Petiole rachis:

*Color.*—Green Group 138A.

*Underneath.*—Smooth, with a few small prickles.

*Stipitate glands.*—Limited numbers present on margins.

Leaflets:

*Size.*—Average size of the terminal leaflet is 35–40 mm(l)×25 mm(w).

*Shape.*—Ovate. Leaflet base: Rounded. Leaflet apex: Acute.

*Margins.*—Serrated.

*Texture.*—Glossy. Leathery.

Hips/seed formation: None observed.

Winter hardiness observation: To date, the new variety has been grown successfully in Zone 5.

Disease resistance: Very good resistance to black spot, powdery mildew, and rust diseases under normal growing conditions.

I claim:

1. A new and distinct variety of rose plant characterized by the following combination of characteristics:

(a) forms attractive, long lasting copper yellow flowers;

(b) exhibits vigorous climbing growth habit;

(c) propagates well using traditional methods, and;

(d) exhibits very good resistance to disease under normal growing conditions;

substantially as herein illustrated and described.

* * * * *

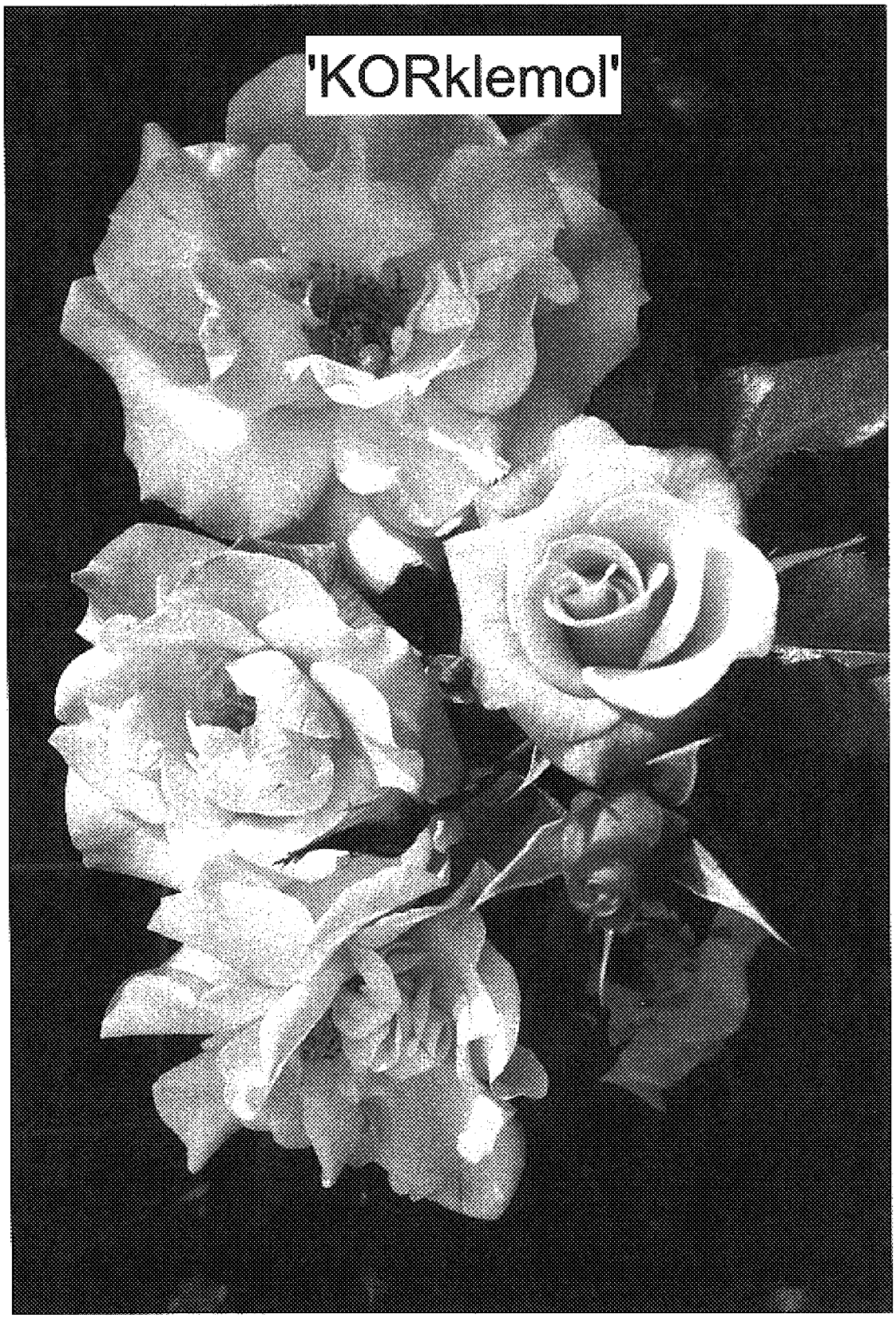
'KORklemol'